US009487820B2

(12) United States Patent
Zhong (10) Patent No.: US 9,487,820 B2
(45) Date of Patent: Nov. 8, 2016

(54) METHODS OF NUCLEIC ACID LIQUID-PHASE EXTRACTION AND DETECTION

(75) Inventor: Haohao Zhong, Beijing (CN)

(73) Assignee: Peking University, Beijing (CN)

( * ) Notice: Subject to any disclaimer, the term of this patent is extended or adjusted under 35 U.S.C. 154(b) by 180 days.

(21) Appl. No.: 14/113,244

(22) PCT Filed: Apr. 27, 2011

(86) PCT No.: PCT/CN2011/000746
§ 371 (c)(1),
(2), (4) Date: Dec. 12, 2013

(87) PCT Pub. No.: WO2012/145861
PCT Pub. Date: Nov. 1, 2012

(65) Prior Publication Data
US 2014/0087388 A1    Mar. 27, 2014

(51) Int. Cl.
*C12Q 1/68* (2006.01)
(52) U.S. Cl.
CPC .................................. *C12Q 1/6806* (2013.01)
(58) Field of Classification Search
None
See application file for complete search history.

(56) References Cited

U.S. PATENT DOCUMENTS 8,877,918 B2 * 11/2014 Ozeki ...................... C12N 1/06
                                                    536/25.4

FOREIGN PATENT DOCUMENTS

| JP | 42-12679 | 7/1942 |
| JP | H05192147 A | 8/1993 |
| JP | 2009254384 A | 11/2009 |

OTHER PUBLICATIONS

Arslan, A. et al., "Effect of method of cooking on identification of heat processed beef using polymerase chain reaction (PCR) technique", Meat Science, 2006, vol. 72, pp. 326-330.
Aslan, Ö. et al., "Integrity of nuclear genomic deoxyribonucleic acid in cooked meat: Implications for food traceability", J. Anim. Sci., 2009, vol. 87: pp. 57-61.
Chung, J.-Y. et al., "A pressure cooking-based DNA extraction from archival formalin-fixed, paraffin-embedded tissue", Analytical Biochemistry, 2012, vol. 425, pp. 128-134.
Coates, P.J. et al., "Simplified procedures for applying the polymerase chain reaction to routinely fixed paraffin wax sections", J. Clin. Pathol., 1991, vol. 44, pp. 115-118.
English Translation of the Examination Report of the German Patent and Trade Mark Office corresponding to German Application No. 11 2011 105 191.3, Mailing Date Feb. 6, 2014, 1 page.

Examination Report of the German Patent and Trade Mark Office corresponding to German Application No. 11 2011 105 191.3, Mailing Date Feb. 6, 2014, 5 pages.
Ferrari, H.F. et al., "Detection of bovine *Herpesvirus* type 5 in formalin-fixed, paraffinembedded bovine brain by PCR: a useful adjunct to conventional tissue-based diagnostic test of bovine encephalitis", Journal of Virological Methods, 2007, vol. 146, pp. 335-340.
Fowler, C. et al., "Modeling formalin fixation and histological processing with ribonuclease A: effects of ethanol dehydration on reversal of formaldehyde cross-links", Laboratory Investigation, 2008, vol. 88, pp. 785-791.
Hennig, G. et al., "Automated Extraction of DNA and RNA from a Single Formalin-Fixed Paraffin-Embedded Tissue Section for Analysis of Both Single-Nucleotide Polymorphisms and mRNA Expression", Clinical Chemistry, 2010, vol. 56, No. 12, pp. 1845-1853.
Murase, T. et al., "Influence of Histochemical and Immunohistochemical Stains on Polymerase Chain Reaction", Mod. Pathol., 2000, vol. 13, No. 2, pp. 147-151.
Sepp, R. et al., "Rapid techniques for DNA extraction from routinely processed archival tissue for use in PCR", J. Clin. Pathol., 1994, vol. 47, pp. 318-323.
Shi, S.-R. et al., "DNA extraction from archival formalin-fixed, paraffin-embedded tissues: heat-induced retrieval in alkaline solution", Histochem. Cell Biol., 2004, vol. 122, pp. 211-218.
Stein, A. et al., "A simple method for amplification of DNA from paraffin-embedded tissues", Nucleic Acids Research, Aug. 17, 1992, vol. 20, No. 19, pp. 5237-5238.
Zhong, H. et al., "Deparaffinization and Lysis by Hydrothermal Pressure (Pressure Cooking) Coupled With Chaotropic Salt Column Purification: A Rapid and Efficient Method of DNA Extraction From Formalin-fixed Paraffin-embedded Tissue", Diagn. Mol. Pathol., Mar. 2013, vol. 22, No. 1, pp. 52-58.
First Office Action corresponding to Chinese Application No. 201180049214.2 issued Jul. 10, 2014.
Shi et al., "DNA Extraction from Archival Formalin-fixed, Paraffin-embedded Tissue Sections Based on the Antigen Retrieval Principle: Heating Under the Influence of pH", J. Histochem. Cytochem. 50:1005-1011 (2002).
Tian et al., "Comparison of three methods of DNA extraction from formaldehyde-fixed, paraffin-embedded tissues," Basic Medical Sciences and Clinics 24:335-338 (2004).

(Continued)

*Primary Examiner* — David Thomas
(74) *Attorney, Agent, or Firm* — Myers Bigel & Sibley, P.A.

(57) ABSTRACT

The invention discloses a method of extracting nucleic acid analyte solution from biological sample, comprising: placing the biological sample into a heating container; optionally, adding solvent medium into the biological sample; heating the biological sample under high pressure; optionally, centrifuging the biological sample; and obtaining the solution including the nucleic acid analyte. The invention also discloses a method of detecting the nucleic acid analyte obtained by said extraction method.

12 Claims, 4 Drawing Sheets

(56) References Cited

OTHER PUBLICATIONS

Wang, "Development and application of an ultra-fast DNA extraction method of pathogenic microorganism", Chinese Journal of Health Laboratory Technology 19:1979-1981 (2009).
PCT/CN2011/000716 International Search Report mailed Feb. 9, 2012.
Office Action corresponding to German Application No. 11 2011 105 191.3 issued Jul. 1, 2015.
Decision of Rejection corresponding to Japanese Application No. 2014-506706 issued Aug. 25, 2015.
Office Action corresponding to Canadian Application No. 2,834,113 issued Feb. 26, 2015.
Office Action corresponding to Chinese Application No. 201180049214.2 issued Mar. 31, 2015.
Office Action corresponding to German Application No. 11 2011 105 191.3 issued Nov. 9, 2015.
Third Office Action corresponding to Chinese Application No. 201180049214.2 issued Oct. 27, 2015.
Shi et al. "DNA Extraction from Archival Formalin-fixed, Paraffin-embedded Tissue Sections Based on the Antigen Retrieval Principle: Heating Under the Influence of pH", *J. Histochemistry & Cytochemistry* 50(8):1005-1011 (2002).
First Office Action corresponding to Japanese Application No. 2014-506706 issued Jan. 27, 2015.
Office Action corresponding to Canadian Application No. 2,834,113 issued Mar. 9, 2016.
Office Action corresponding to Chinese Application No. 201180049214.2 issued May 23, 2016.

\* cited by examiner

(1) (5) 575bp   (2)(6)(8) 241bp   (3)(7)(9)192bp   (4)100bp Marker

Comparison table indicating the relationship between the temperature and pressure of the saturated vapor

| Temperature °C | 22 | 24 | 26 | 28 | 30 | 32 | 34 | 36 | 38 | 40 |
|---|---|---|---|---|---|---|---|---|---|---|
| Vapor pressure MPa | 0.00264 | 0.00298 | 0.00336 | 0.00378 | 0.00424 | 0.0048 | 0.00532 | 0.00594 | 0.0066 | 0.00738 |
| Temperature °C | 42 | 44 | 46 | 48 | 50 | 52 | 54 | 56 | 58 | 60 |
| Vapor pressure MPa | 0.0082 | 0.0091 | 0.01009 | 0.01116 | 0.01234 | 0.0136 | 0.015 | 0.01651 | 0.0182 | 0.01992 |
| Temperature °C | 62 | 64 | 66 | 68 | 70 | 72 | 74 | 76 | 78 | 80 |
| Vapor pressure MPa | 0.02184 | 0.02391 | 0.02615 | 0.02856 | 0.03116 | 0.034 | 0.03696 | 0.04019 | 0.0437 | 0.04736 |
| Temperature °C | 82 | 84 | 86 | 88 | 90 | 92 | 94 | 96 | 98 | 100 |
| Vapor pressure MPa | 0.05133 | 0.05557 | 0.06011 | 0.06495 | 0.07011 | 0.0756 | 0.08146 | 0.08769 | 0.0943 | 0.10133 |
| Temperature °C | 102 | 104 | 106 | 108 | 110 | 112 | 114 | 116 | 118 | 120 |
| Vapor pressure MPa | 0.10878 | 0.11668 | 0.12504 | 0.1339 | 0.14327 | 0.1532 | 0.16362 | 0.17465 | 0.1863 | 0.19854 |
| Temperature °C | 122 | 124 | 126 | 128 | 130 | 132 | 134 | 136 | 138 | 140 |
| Vapor pressure MPa | 0.21145 | 0.22504 | 0.23933 | 0.25436 | 0.27013 | 0.2783 | 0.30407 | 0.32229 | 0.3414 | 0.36138 |
| Temperature °C | 145 | 150 | 155 | 160 | 165 | 170 | 175 | 180 | 185 | 190 |
| Vapor pressure MPa | 0.4155 | 0.476 | 0.5433 | 0.6181 | 0.7008 | 0.792 | 0.8924 | 1.0027 | 1.1233 | 1.2551 |

Figure 6

METHODS OF NUCLEIC ACID LIQUID-PHASE EXTRACTION AND DETECTION

RELATED APPLICATIONS

This application is a 35 U.S.C. §371 national phase application of PCT Application PCT/CN2011/000746 filed Apr. 27, 2011. The entire content of this application is incorporated herein by reference.

FIELD OF THE INVENTION

The present invention relates to nucleic acid extraction and detection, and more particularly, the present invention relates to methods for liquid-phase releasing of nucleic acids from a biological sample and detection thereof by using high-pressure heating.

BACKGROUND OF THE INVENTION

Gene detection plays an increasingly important role in modern clinical medicine. The first step in gene detection is to extract nucleic acids from a fixed or non-fixed biological sample.

According to conventional chemical methods, cells or tissues are usually first digested with enzymes, and then extracted with organic solvents. The isolated nucleic acids are precipitated by ethanol or isopropanol, collected and concentrated in water. The whole process takes 2-3 days. Especially for paraffin-embedded tissue, there are additional needs for multiple dewaxing in xylene, long-term digestion with high concentration of proteases and the like, resulting in more prominent disadvantage of low time efficiency.

In recent years, a variety of solid-phase nucleic acid extraction kits are developed at home and abroad. Most of such kits are based on the principle of lysing cell to release the nucleic acids, adsorbing the nucleic acids to the surface of certain particles, and then precipitating or eluting. These processes result in relatively shortened nucleic acid extraction time, but are still far from the low-cost, high-efficient, simple target processes.

With the increasing importance of gene detection, nucleic acid extraction technology has not undergone simultaneous innovation and breakthrough compared with the emergence of the new method and technology in gene detection. Availability of qualified nucleic acid has become the key to the success of gene detection, especially for genotyping or diagnosis highly dependent on the paraffin-embedded tissue.

SUMMARY OF THE INVENTION

The present invention provides a method for extracting nucleic acid analyte solutions from a biological sample, the method comprising the steps of: placing the biological sample in a heating container; optionally, adding a dissolution medium into the biological sample; subjecting the biological sample to high-pressure heating; optionally, centrifuging the biological sample; and obtaining a liquid containing said nucleic acid analyte.

The method of the present invention is particularly suitable for extracting nucleic acids from formalin-fixed paraffin-embedded tissue. In this method, the dewaxing of the paraffin-embedded tissue, the lysing of the tissue cells, and the de-crosslinking are completed simultaneously through the single high-pressure heating step, until the liquid-phase nucleic acids are released.

The present invention further provides a method for the detection of a nucleic acid analyte in a biological sample, comprising obtaining a solution of said nucleic acid analyte according to the method of the present invention, and detecting the nucleic acid analyte, preferably by polymerase chain reaction (PCR).

The method of the present invention is simple (for example, the most commonly used nucleic acid extraction kits require more than 20 steps), time-saving, and low-cost, and does not require special equipments and reagents. The simple operation method is easy to carry out, greatly improving the efficiency of the preparation and detection of a nucleic acid solution.

DETAILED DESCRIPTION OF THE INVENTION

The present invention provides in one aspect a method for extracting nucleic acid analyte solutions from a biological sample, the method comprising the steps of: placing the biological sample in a heating container; optionally, adding a dissolution medium into the biological sample; subjecting the biological sample to high-pressure heating; optionally, centrifuging the biological sample; and obtaining a liquid containing said nucleic acid analyte. Typically, the nucleic acid analyte solution can be directly used for subsequent detection, such as PCR. This greatly simplifies the steps of nucleic acid extraction.

As used herein, the term "nucleic acid analyte" refers to the target nucleic acid molecule to be analyzed, including DNA and RNA. When the nucleic acid to be analyzed in the sample is a housekeeping gene, the solution thus obtained has a higher nucleic acid content due to the large copy number of the nucleic acid, which facilitates the subsequent PCR detection. When the copy number of the nucleic acid to be analyzed is low, the nucleic acid solution can be further concentrated after it is obtained using the method of the present invention, such as a concentration by chromatographic column so as to improve the concentration of nucleic acids.

As used herein, the term "optionally" means "left to choice" or "non-essential". "Optionally, centrifuging the sample" means that a centrifugation may or may not be carried out, which may be selected by persons skilled in the art according to circumstances.

As used herein, the term "high pressure" refers to a higher pressure than the standard atmospheric pressure. For example, the air pressure at sea level under standard atmospheric conditions represents one atmospheric pressure, roughly equivalent to 101.3 kPa.

The "high pressure" in the present invention can be achieved by high-pressure equipments commonly used in the art, such as a pressure cooker, an electric pressure cooker, an autoclave, and the like.

Figure 6:
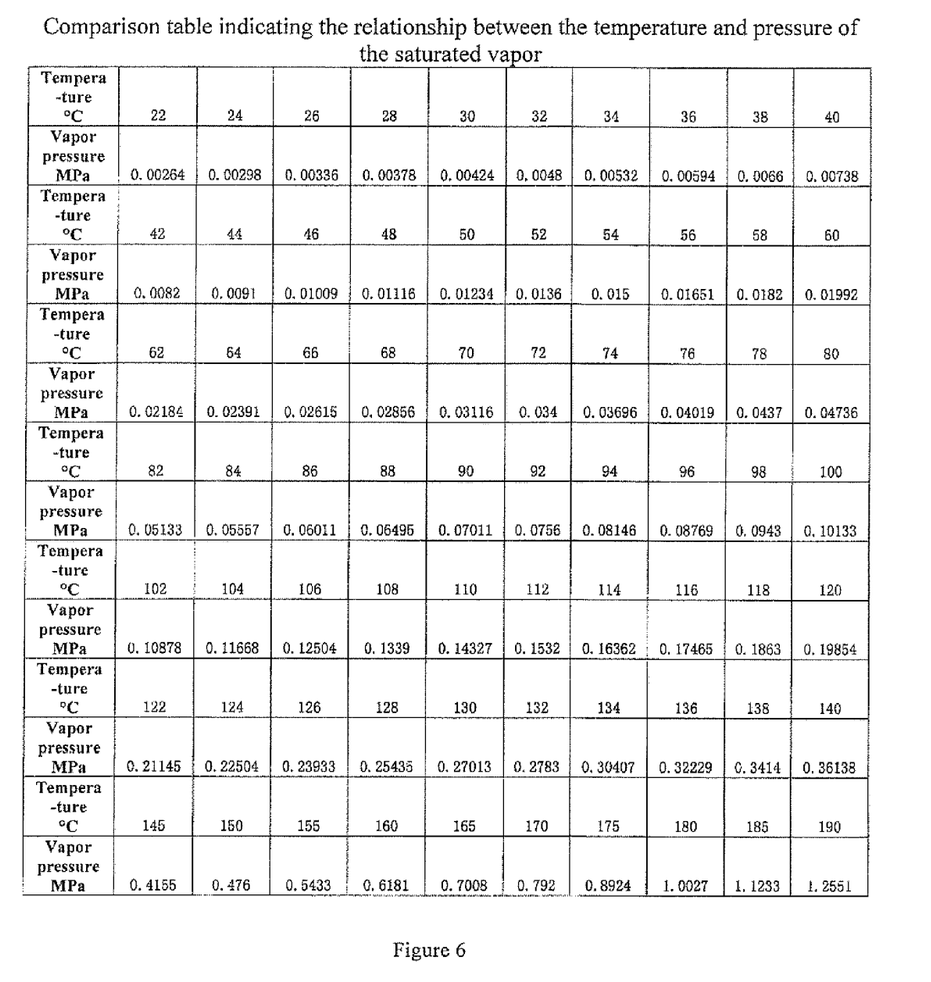
FIG. 6 shows the comparison table indicating the relationship between the temperature and pressure of the saturated vapor.

The most common used high-pressure equipments are steam heating equipments. It is well known in the art that the temperature during high-pressure heating is usually higher than that during the normal-pressure heating. There are several methods in the art for estimating the relationship between the pressure and the temperature during the high-pressure heating (see, e.g., "the comparison table indicating the relationship between the temperature and pressure of the saturated vapor" as shown in FIG. 6). According to these methods, one can roughly estimate the approximate temperature during high-pressure heating. For example, when the pressure of the steam pressure cooker is 250 kPa, the temperature is about 127° C.

The "high pressure" in the present invention is typically 105 kPa or more, for example 110 kPa, 115 kPa. The upper limit of the pressure of the commonly used steam pressure cooker is approximately 350 kPa.

The "high pressure" used in the method of the present invention can be between 105-350 kPa, such as 110-320 kPa, particularly 115-250 kPa, preferably 120-200 kPa.

Different biological samples vary from each other in terms of the tolerance to temperature and pressure. Those skilled in the art can find optimized high-pressure temperature and time by routine experimentation according to the nature of the sample to be tested. For example, when the sample can easily be dissolved (for example, tumor or virus samples), heating pressure and time can be reduced; when the biological sample is difficult to dissolve (e.g., *Candida albicans*), heating pressure and time can be increased.

The heating time can be in the range of 5-210 minutes in view of different samples and different pressures, for example 10-90 minutes. In particular, the commonly used heating time is 20-60 minutes. The skilled person would appreciate that, when the heating pressure is low and the nucleic acid in the sample is difficult to be released, a longer heating time could be used, such as four hours.

For example, when a paraffin-embedded tissue section sample is to be processed, the typical heating condition may be: maintaining 25-45 minutes under the pressure of 140-170 kPa. When a *Candida albicans* sample is to be processed, the typical heating condition may be: maintaining 45-60 minutes under the pressure of 140-170 kPa.

As used herein, the term "biological sample" refers to those containing nucleic acid to be tested, including those biological samples from animals, plants, microorganisms or human bodies. Biological samples may be various fresh, frozen or fixed samples, such as tissue biopsy samples, tumor samples, formalin-fixed paraffin-embedded tissue samples, as well as microorganisms sample such as bacteria, fungi, viruses, mycoplasma and the like. Common fresh biological samples include: biological fluid samples, such as blood, serum, tissue fluid, urine, stool, sputum, cerebrospinal fluid, saliva, tears, nipple aspirate fluid and cultured cells; tumor samples, such as diseased tissues to removed from a subject; and the like. A typical fixed biological sample is a 10% formalin-fixed paraffin-embedded tissue. The method of the invention is particularly suitable for paraffin-embedded tissue samples, including longer-term paraffin blocks and sections kept in the archives.

During the heating of biological samples, the samples can be placed in a heating vessel. Commonly used heating vessels include centrifuge tubes and tubes, for example, a 1.5 mL or 10 mL centrifuge tube with cap. Preferably, the tube cap is perforated so as to prevent uncapping due to the expansion of the gas during high-pressure heating. Samples can also be placed in a gauze-sealed Erlenmeyer flask or flask, or other gas-permeable containers for heating.

Before the high-pressure heating, an optional dissolution medium may be added into the biological sample as required. For example, before heating paraffin-embedded tissue sections, 0.1 M NaOH solution, for example, 200 µl or 1 ml, may be added such that the samples are completely immersed in the liquid. The commonly used dissolution media include water, DEPC-treated water, physiological saline, alkaline solution, buffer solution and the like. Commonly used buffer solutions include Tris-HCl buffers, phosphate buffers, acetic acid-sodium acetate buffers, glycine-HCl buffers, disodium hydrogen phosphate-sodium citrate buffer solutions and citric acid-sodium citrate buffer solutions, etc. Those skilled in the art would appreciate that, when the biological samples per se already contain a large amount of liquid (for example cerebrospinal fluids), no additional dissolution media may be added.

After the high-pressure heating step, the samples may be optionally centrifuged to obtain supernatants. Nucleic acid is usually dissolved in the supernatant and can be directly used for subsequent operations, such as PCR. Those skilled in the art would appreciate that, the centrifugation step is not indispensable. When the omission of the centrifugation of the nucleic acid solution has no effect on subsequent experiments (e.g., PCR), the centrifugation may not be needed.

In a preferred embodiment of the present invention, the following steps are included: optionally, perforating the cap of the centrifuge tube; placing the paraffin-embedded tissue sections (for example, 1-2 sections) in the centrifuge tube, and adding pure water or alkaline solution (e.g., NaOH solution), such that the samples are immersed in the liquid; heating said samples under the pressure of 140-200 kPa for 25-45 minutes; and centrifuging the samples to obtain supernatants. The supernatant can be directly used in the subsequent PCR reaction.

Another aspect of the present invention relates to providing a method to detect a nucleic acid analyte in a biological sample, comprising obtaining a solution of the nucleic acid analyte according to the method as described above, and detecting the nucleic acid analyte. In a particularly preferred embodiment, the detection is carried out by polymerase chain reaction (PCR).

The present invention will be further illustrated with reference to the following Examples. These examples are provided to facilitate the understanding of the present invention, and shall not be construed as constraining the application of the present invention.

EXAMPLES

Example 1

Gene Detection of Human Colon Cancer K-Ras Exon 2

1. Preparation of the centrifuge tube: The cap of a 1.5 ml centrifuge tube was perforated a tiny pore by a fine needle heated using alcohol burner, so as to prevent uncapping due to the expansion of the gas during the high-pressure process.

2. Sampling: One to two pieces of human colon cancer paraffin-embedded tissue sections (5-10 μm) were placed into a 1.5 ml centrifuge tube. 500 μl of 0.1 M NaOH solution (pH 11) was added, such that the sample was completely immersed in the liquid.

3. High pressure: High-pressure heating was performed for 30-45 minutes (LIREN brand electric pressure cooker, Model DYG-5B, pressure of 140-170 kPa, pressure limit of 200 kPa).

4. PCR: A centrifugation step (13,000 rpm, 5 minutes) was immediately carried out without cooling after the high-pressure process was completed. One to two μl of the supernatant (or 1-2 μl of the 1:10 dilution of the supernatant) was used Ts for PCR analysis in accordance with the instructions.

5. Electrophoresis: The PCR products were detected by electrophoresis. If the amount of the products was too small, a nested PCR could be carried out.

Figure 1A:
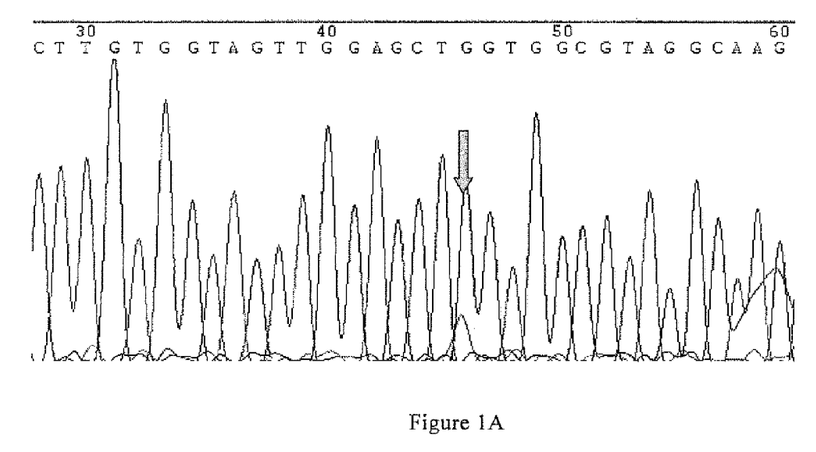
FIG. 1A shows the point mutation at codon 12 (G12S) of K-ras exon 2, 5'→3'.
Figure 1B:
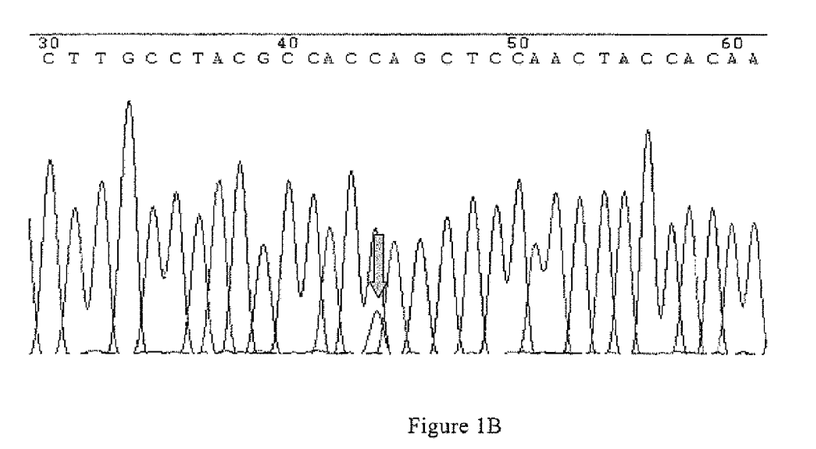
FIG. 1B shows the reverse sequencing results of the same specimen (3'→5'). The arrows indicate the mutation points.

6. The sequencing result of the PCR products: See, FIG. 1A and FIG. 1B.

The results showed that the nucleic acid sample obtained from the paraffin-embedded tissue sample through the method of high-pressure heating fully meets the requirements of direct sequencing of the PCR products.

Example 2

Gene Detection of Human Colon Cancer
(Laser-Microdissected Tumor Cells) K-Ras Exon 2

Figure 2:
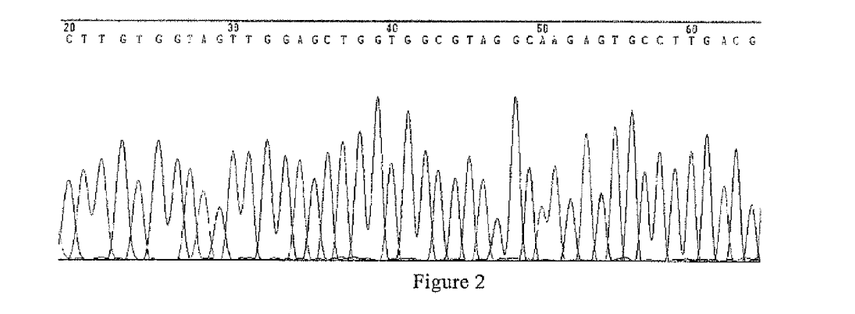
FIG. 2 shows the normal sequence of codons 12, 13 of human colon cancer K-ras exon 2.

Certain amount of laser-microdissected tumor cells of paraffin sections were processed according to the method of Example 1 (if the amount of the cells was small, the amount of solution could be reduced). The supernatant was used for PCR. The sequencing results of the PCR products were shown in FIG. 2.

The aforesaid results showed that the high-pressure heating method of the present invention is applicable to small amount of cells for obtaining nucleic acids of reliable quality which could be used for genotyping analysis and diagnosis. The success rate for genotyping analysis and diagnosis of small amount of cells or tissues (such as fine needle aspiration tumor tissues) was increased, which is of great significance for cancer patients who had missed the opportunity of surgery to select drugs for the treatment.

Example 3

The Nucleic Acid Amplification Detection of
*Mycobacterium tuberculosis* in Paraffin-Embedded
Tissues One to two pieces of paraffin-embedded tissue sections suspected of infection by *Mycobacterium tuberculosis* were processed according to essentially the same method as that of Example 1, wherein the heating time is 20-30 minutes. The supernatant was used for Real-time PCR (fluorescent probes were added in the PCR pre-mix).

The results showed that, bacterial DNAs with acceptable quality could be obtained from paraffin-embedded tissues by the high-pressure heating method, assisting in the clinical identification and diagnosis of the *Mycobacterium tuberculosis* infection.

Example 4

Gene Detection of *Candida Albicans*

Figure 3:
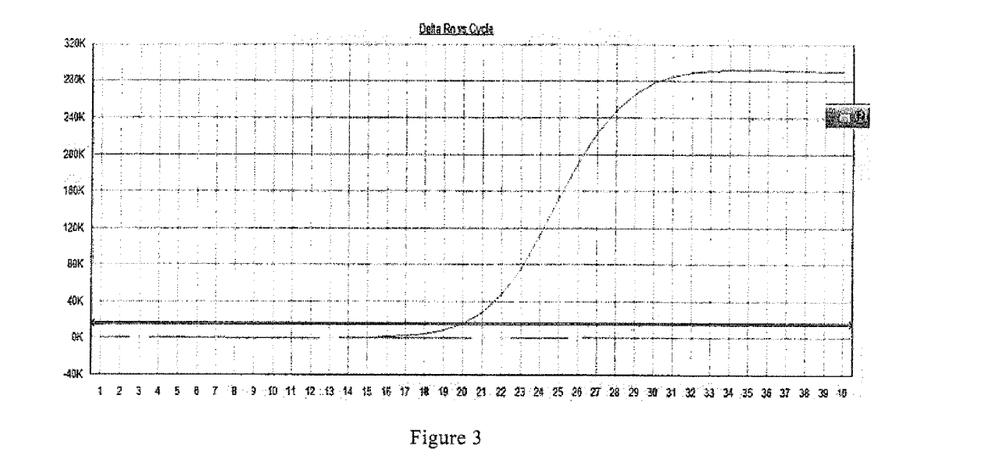
FIG. 3 shows the result of fluorescent PCR for *Candida albicans*, wherein the vertical coordinate represents the amount of fluorescence, and the horizontal coordinate represents the number of PCR cycles. The two curves represent positive results.

Swabs for human lesion suspected of *Candida albicans* infection were washed in 200 μl of 0.1 M NaOH solution (pH 11), and then were processed according to essentially the same method as that of Example 1, wherein the heating time is 35-50 minutes. The supernatant was used for fluorescent PCR (fluorescent probes were added in the PCR pre-mix). The results were shown in FIG. 3. *Candida albicans* belongs to fungi and is several times to tens of times larger than a bacterium. The very thick cell walls were difficult to be disrupted by general approaches during experiments, thus affecting the sensitivity of PCR. In recent years, fungal infections increased significantly, which was related to dysbacteriosis resulted from the abuse of antibiotics and immunodeficiency resulted from the administration of hormones and anticancer drugs. There are many types of pathogenic fungi, and the drug tolerance thereof is different from each other. It is currently more accurate to distinguish between different types of fungi from gene sequences.

The aforesaid results showed that, for fungi with thick and firm cell walls, the high-pressure heating method was of great advantages as it can easily obtain nucleic acid with reliable quality so as to distinguish the gene sequence and directly identify the types of fungi.

Example 5

Detection of HBV Viruses in Human Serum

Figure 4:
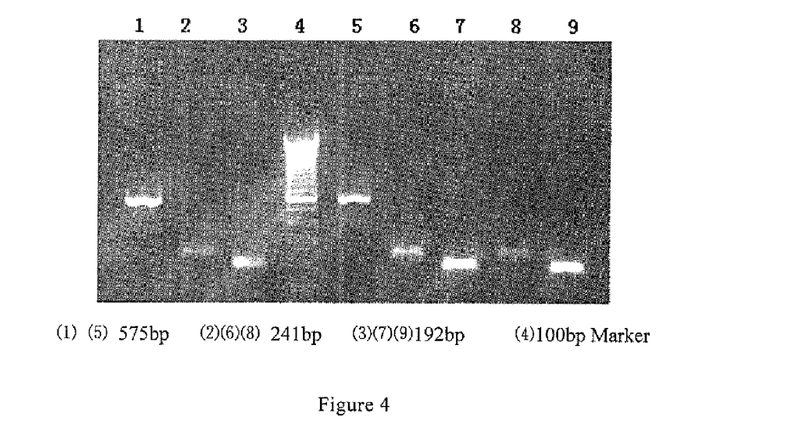
FIG. 4 shows the electrophoretic results of the 575, 241, and 192 bp HBV specific fragment sequences of human serum HBV virus.

5 μl of serum from an HBV patient was mixed with 200 μl of 0.1 M NaOH solution (pH 11), and then was processed according to essentially the same method as that of Example 1, wherein the heating time is 25-40 minutes. The supernatant was used for PCR. Electrophoresis results were shown in FIG. 4.

The aforesaid results showed that the high-pressure heating method could be used to obtain viral nucleic acids with reliable quality from trace amount of serum for clinical testing.

Example 6 mRNA Detection in Fresh Tissues,
Paraffin-Embedded Tissues, and Cultured Cells

1. Sampling:
a. paraffin sections of human gastrointestinal stromal tumor (5-10 μm), 1-2 pieces
b. paraffin-embedded tissues of human colon cancer (5-10 μm), 1-2 pieces
c. fresh tissues of human thyroid cancer (½ grain size), minced
d. cultured cells The samples were placed in a 1.5 ml centrifuge tube. An appropriate amount of 0.1 M NaOH solution (pH 11) was added such that the samples are completely immersed in the liquid. The resulting solution was thoroughly mixed.

2. High pressure: Heating time was 30-45 minutes (pressure of 140-170 kPa, pressure limit of 200 kPa).

3. Reverse transcription: (During the RNA extraction, timely high-pressure processes were needed and reverse transcription pre-mix shall be prepared beforehand) When the high-pressure process was completed, the centrifuge tube was uncapped after an instant centrifugation, and 2-5 μl supernatant was quickly used for reverse transcription so as to prevent rapid degradation of the RNA.

Reverse transcription pre-mix: 1× reverse transcription buffer, 0.2 mM dNTPs, 0.2 μg random primers (or 0.2 μM specific primers), 50 U M-mLV reverse transcriptase, 0.01 M DTT, DEPC water added to a final volume of 20 μl.

42° C. for 60 minutes, 95° C. for 5 minutes.

4. PCR: After the reverse transcription was completed (an instant centrifugation could be carried out), 1-5 μl of the supernatant was added to the PCR pre-mix (containing 1×PCR buffer, 0.2 mM dNTPs, 0.4-0.5 μM specific primers, water added to a final volume of 25-50 μl). PCR: 94° C. for 1 minute 30 seconds, (94° C. for 30 seconds, 55° C. for 30 seconds, 72° C. for 20 seconds, 30-35 cycles), 72° C. for 2 minutes.

Figure 5:
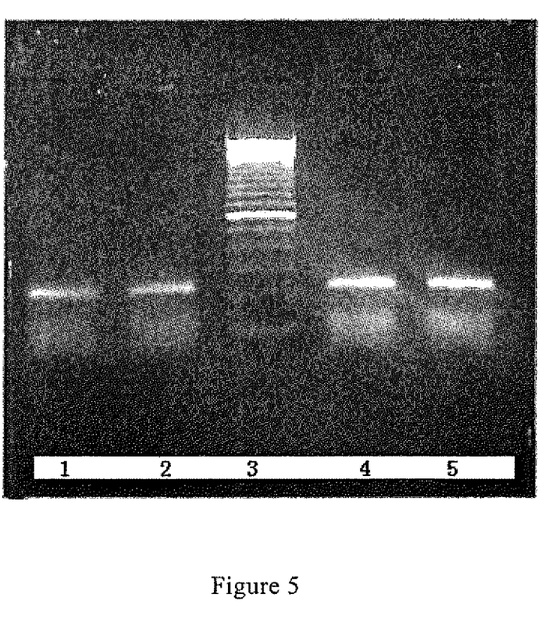
FIG. 5 shows an electropherogram: [1] paraffin-embedded tissues of human gastrointestinal stromal tumor; [2] paraffin-embedded tissues of human colon cancer; [3] 100 bp markers; [4] fresh tissues of human thyroid cancer; [5] cultured cells.

5. The results of GAPDH mRNA RT-PCR (electropherogram-226 bp): See FIG. 5.

The aforesaid results showed that high-pressure heating method could be used to simultaneously obtain DNA and RNA with reliable quality, and could also be used for the detection of specific gene sequence fragments (DNA) and biological markers (mRNA).

Example 7

Effects of Different Temperature and High Pressure on the Nucleic Acid Releasing of Biological Samples 1. The centrifuge tube was prepared in accordance with the same method as that in Example 1.
2. Sampling
(1) 5 μl of serum from HBV patient was mixed with 100 μl of 0.1 M NaOH solution (pH 11).
(2) Swabs for HSV patient were washed in 100 μl of 0.1 M NaOH solution (pH 11).
(3) Two pieces of 7 μM paraffin-embedded tissue sections from tumor patient were added to 500 μl of 0.1 M NaOH solution (pH 11).
3. The types of the pressure cooker
(1) LIREN brand electric pressure cooker, Model DYG-5B
(2) Taiwan CIRRUS CR-3560CG-M autoclave
4. The method The aforesaid three biological samples were subject to high-pressure processing by using LIREN brand electric pressure cooker (Model DYG-5B) and Taiwan CIRRUS CR-3560CG-M autoclave respectively at different temperatures for different time.

5. The results

The results were shown in Table 1. The experimental results showed that different biological samples varied in terms of the tolerance to the time and the pressure of high-pressure processing.

TABLE 1

| Name of the sample | Type of the pressure cooker | Heating time (minutes) | Heating temperature (° C.) | PCR results |
|---|---|---|---|---|
| HSV II (herpes simplex virus II) human swabs | LIREN brand electric pressure cooker | 30 | 115° C. | + |
| | | 60 | 115° C. | + |
| | | 90 | 115° C. | − |
| | | 210 | 115° C. | − |
| | autoclave | 5 | 130° C. | + |
| | | 10 | 130° C. | − |
| | | 15 | 130° C. | − |
| HBV (serum) | LIREN brand electric pressure cooker | 30 | 115° C. | + |
| | | 60 | 115° C. | + |
| | | 90 | 115° C. | + |
| | | 210 | 115° C. | + |
| | autoclave | 5 | 130° C. | + |
| | | 10 | 130° C. | − |
| | | 15 | 130° C. | − |
| | | 120 | 130° C. | − |
| paraffin-embedded tissue (β-actin) | LIREN brand electric pressure cooker | 30 | 115° C. | + |
| | | 60 | 115° C. | + |
| | | 90 | 115° C. | + |
| | | 210 | 115° C. | − |
| | autoclave | 5 | 130° C. | + |
| | | 10 | 130° C. | + |
| | | 15 | 130° C. | + |
| | | 30 | 130° C. | + |
| | | 120 | 130° C. | + |

Note:
In the column of "PCR results", "+" indicates positive, and "−" indicates negative.

The invention claimed is:

1. A method for extracting nucleic acid analyte solutions from a biological sample, the method comprising the steps of: placing the biological sample in a heating container; optionally, adding a dissolution medium into the biological sample; subjecting the biological sample to high-pressure heating; optionally, centrifuging the biological sample; and obtaining a liquid containing said nucleic acid analyte, wherein said high-pressure is 105-170 kPa, and the duration time of said high-pressure heating step is 5-45 minutes.

2. The method of claim 1, wherein said biological sample is selected from the group consisting of biopsy samples, cell samples, tumor samples, and biological fluid samples.

3. The method of claim 2, wherein said biological fluid sample is selected from the group consisting of blood, serum, tissue fluid, urine, stool, sputum, cerebrospinal fluid, saliva, tears, and nipple aspirate fluid.

4. The method of claim 1, wherein said biological sample is a paraffin-embedded tissue.

5. The method of claim 1, wherein the dissolution medium is selected from the group consisting of water, DEPC-treated water, physiological saline, alkaline solution, and buffer solution.

6. The method of claim 4, comprising the steps of;
optionally, perforating the cap of a centrifuge tube;
placing the paraffin-embedded tissue sections in the centrifuge tube, and adding pure water, or alkaline solution, such that the samples are immersed in the liquid;
heating said samples under the pressure of 140-170 kPa for 25-45 minutes; and
centrifuging the samples to obtain supernatants.

7. A method for the detection of a nucleic acid analyte in a biological sample, comprising
obtaining a solution of said nucleic acid analyte according to the method of claim 1, and
detecting the nucleic acid analyte.

8. The method of claim 7, wherein said detection is carried out by polymerase chain reaction.

9. The method of claim 7, further comprising concentrating the solution of said nucleic acid analyte.

10. The method of claim 1, wherein said high-pressure is 140-170 kPa, and the duration time of said high-pressure heating step is 30-45 minutes.

11. The method of claim 1, wherein the nucleic acid analyte is RNA, said high-pressure is 140-170 kPa, and the duration time of said high-pressure heating step is 30-45 minutes.

12. The method of claim 1, wherein the nucleic acid analyte is DNA, and said biological sample is not a formalin-fixed paraffin-embedded tissue.

* * * * *

UNITED STATES PATENT AND TRADEMARK OFFICE
CERTIFICATE OF CORRECTION

Page 1 of 1

PATENT NO. : 9,487,820 B2
APPLICATION NO. : 14/113244
DATED : November 8, 2016
INVENTOR(S) : Zhong It is certified that error appears in the above-identified patent and that said Letters Patent is hereby corrected as shown below:

In the Specification

Column 5, Line 16: Please correct "was used Ts for PCR" to read -- was used for PCR --

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*